(12) United States Patent
Luo et al.

(10) Patent No.: US 7,939,906 B2
(45) Date of Patent: May 10, 2011

(54) PREPARATION METHOD FOR AN ELECTRON TOMOGRAPHY SAMPLE WITH EMBEDDED MARKERS AND A METHOD FOR RECONSTRUCTING A THREE-DIMENSIONAL IMAGE

(75) Inventors: Jian-Shing Luo, Taoyuan County (TW); Chia-Chi Huang, Taichung County (TW)

(73) Assignee: Inotera Memories, Inc., Taoyuan County (TW)

( * ) Notice: Subject to any disclaimer, the term of this patent is extended or adjusted under 35 U.S.C. 154(b) by 196 days.

(21) Appl. No.: 12/471,734

(22) Filed: May 26, 2009

(65) Prior Publication Data

US 2010/0084555 A1    Apr. 8, 2010

(30) Foreign Application Priority Data

Oct. 3, 2008    (TW) ................................. 97138142 A

(51) Int. Cl.
*G01N 23/04*    (2006.01)
*H01L 23/58*    (2006.01)
*H01J 37/26*    (2006.01)

(52) U.S. Cl. ................ 257/486; 257/E21.001; 250/311; 250/304; 427/532; 382/145

(58) Field of Classification Search .................. 257/486, 257/E21.001; 427/532; 250/311, 304; 382/145
See application file for complete search history.

(56) References Cited

U.S. PATENT DOCUMENTS

| 7,538,322 B2 * | 5/2009 | Luo et al. ...................... 250/304 |
| 7,700,944 B2 * | 4/2010 | Nishizawa ...................... 257/48 |
| 2005/0026439 A1 * | 2/2005 | Watanabe et al. ............. 438/691 |

* cited by examiner

*Primary Examiner* — Nikita Wells
(74) *Attorney, Agent, or Firm* — Rosenberg, Klein & Lee

(57) ABSTRACT

A manufacturing method for an electron tomography specimen with embedded fiducial markers includes the following steps. A chip of wafer is provided. The chip includes at least one inspecting area. At least one trench is produced beside the inspecting area. A liquid with the markers is filled into the trenches. A first protection layer is coated on the chip, and then a second protection layer is deposited on the first protection layer. Therefore, the markers can be embedded into the electron tomography specimen. The embedded markers can improve the alignment process, due to those embedded markers are easily tracked during feature tracking procedure. In addition, our novel invention also successfully provides a modified version of the technique to deposit gold beads onto TEM pillar samples for much improved 3D reconstruction.

18 Claims, 2 Drawing Sheets

PREPARATION METHOD FOR AN ELECTRON TOMOGRAPHY SAMPLE WITH EMBEDDED MARKERS AND A METHOD FOR RECONSTRUCTING A THREE-DIMENSIONAL IMAGE

BACKGROUND OF THE INVENTION

1. Field of the Invention

The present invention relates to a preparation method for manufacturing an electron tomography (ET) sample and a method for constructing a three-dimensional (3D) image. In particular, the present invention relates to a preparation method for manufacturing an ET sample with embedded markers and a method for reconstructing a 3D image from series of tilted two-dimensional (2D) transmission electron microscopy (TEM) images.

2. Description of Related Art

The rapid advances in nanotechnology and the decreasing size of features in the microelectronics industry result in the need for advanced characterization with high spatial resolution in two and three dimensions. Therefore, the demands for physical failure and materials analysis using the transmission electron microscope or scanning transmission electron microscope are rapidly increasing: for instance thickness measurement, small defect identification, chemical element analysis, etc. It is well known that sample preparation is a crucial point for successful TEM or STEM analysis. Furthermore, some artifacts, such as amorphous layers and overlapping interfaces in small vias, will become more serious as the dimensions of the TEM sample become larger relative to the ever-shrinking device dimensions. ET provides a solution to characterize nano-scale devices by reconstructing a 3D image from a series of tilted 2D projections. Electron tomography includes four main steps: series of tilted 2D images acquisition, image processing, 3D reconstruction, and visualization. After acquisition, tilt-series alignments are performed to refine the relative image shifts and tilt-axis orientation using image-processing software. The acquired tilt-series must be precisely aligned with the tilt axis to minimize the blurring of small features and artifacts in the reconstruction. Two methods are used to align the tilt-series: cross-correlation and feature tracking. Feature tracking enables the correction of x-y shifts and the average tilt-axis orientation, and also allows image orientation and magnification changes to be measured and compensated. This provides a more accurate image alignment in the case of image distortion comparison with cross-correlation method. For prior art, there are two well-know methods to prepare an ET sample.

The first method is to place a flat and thin specimen onto the carbon-coated grids with fiducial markers. The fiducial markers (i.e., metal particles) are prior deposited on the carbon-coated grids. Then, the TEM specimen is placed on the carbon-coated grids above the metal particles. Those metal particles below the specimen are the references of series tilted 2D images alignment for feature tracking process. However, there is a gap between the specimen and fiducial markers. Therefore, the circular motion paths of fiducial markers are relatively longer during sample tilting compared with each point in the specimen resulting in a change in focus and image shift problems on those fiducial markers during series of tilted 2D images acquisition. Because of the specimen and fiducial markers are not at the same focus plane. That may make fiducial markers difficult to track or even missing in the worst case, especially with higher magnifications, thicker samples and higher tilt angles. In addition, the ET 3D images reconstructed from the traditional flat and thin sections are incomplete because the projection images can not be acquired from the range of directions lying close to the plane of the sample. The lack of information at high tilt angles is referred to as the missing wedge problem.

The second method is to manufacture a cylindrical or pillar specimen. The cylindrical or pillar specimen can be rotated and imaged in full 360 degree range (from 0° to 360°, or from −90° to +90°) with no change in the electron path length through the specimen. However, it is not easy for the user to deposit the metal particles (fiducial markers) onto the pillar specimen for feature tracking process.

The present invention is for preparing ET samples with gold beads inside to improve the feature tracking process and quality of 3D reconstruction.

SUMMARY OF THE INVENTION

One particular aspect of the present invention is to embed fiducial markers in the ET tomography samples so that the markers can be used for aligning series of tilted 2D images to minimize the blurring of small feature and artifacts in the reconstruction without a change in focus and image shift problems. Thereby, the image analysis system can use the markers that are clearly focused and easily tracked as the references to align series of tilted 2D images. The rotation shift offset is to be compensated for reconstructing the 3D image with good quality.

One particular aspect of the present invention is to use the dimension of the markers as a calibration reference to calculate the dimensions of the structures in the specimen.

The present invention provides a sample preparation method for an ET sample, and the sample preparation method includes the following steps. A chip of wafer is provided. The chip includes at least one inspecting area. At least one trench is produced beside of the inspecting area. A liquid with the markers is filled into the trench. A first protection layer is coated on the chip, and a second protection layer is deposited onto the first protection layer.

The present invention also provides a method for reconstructing the 3D images.

The present invention has the following characteristics. The present invention embeds the high contrast markers into the ET samples so that the markers can be used as alignment references for reconstructing the series of tilted 2D images into 3D images. The problems of change in focus and image shift on fiducial markers are overcome and the quality of the 3D reconstruction is improved.

For further understanding of the present invention, the reference is made to the following detailed description illustrating the embodiments and examples of the present invention. The description is for illustrative purpose only and is not intended to limit the scope of the claim.

BRIEF DESCRIPTION OF THE DRAWINGS

The drawings included herein provide a further understanding of the present invention. A brief introduction of the drawings is as follows.

DETAILED DESCRIPTION OF THE PREFERRED EMBODIMENTS

Reference is made to FIGS. 1 to 4; the present invention provides a preparation method to embed the markers into the specimen and a method to reconstruct the 3D image. The markers are embedded into the specimen by the preparation method of the present invention so that the markers can be used as alignment references for reconstructing the 3D image so as to improve the 3D image quality.

The first embodiment of the sample is illustrated as below. The preparation method of an ET sample includes the following steps.

Figure 1:
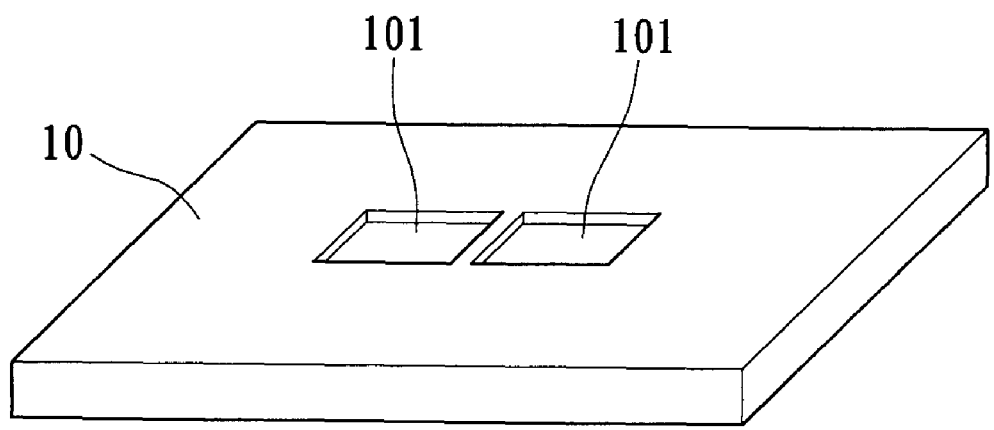
FIG. 1 is a schematic diagram of milling two trenches beside the interesting area on the chip for embedding the markers of the present invention.

Step 1: A chip 10 is provided. The chip 10 includes at least one inspecting area. Reference is made to FIG. 1. In this embodiment, the inspecting area on the chip 10 is a target for the analyst to observe and analyze. The neighborhood of the inspecting area is plane (i.e. with no concave structure) so that the inspecting area does not have the concave structures for receiving adequate markers 11, which is the crucial point to improve the feature tracking process and quality of 3D reconstruction.

Step 2: At least one trench 101 is produced adjacent to the inspecting area. Because there is no concave structure around the inspecting area for receiving the markers, at least one receiving space (i.e. the trench 101) is produced beside the inspecting area. In this embodiment, a dual beam focused ion beam (DB FIB) system is used to mill two square trenches 101 at two sides of the inspecting area. The dimension (length, width, height) of the trench 101 is 2 µm×2 µm×1 µm. The dimension, shape, and location of the trench 101 can be adjusted flexibly according to the requirement.

Step 3: A liquid with the markers 11 is filled into the trenches 101. The goal of the present invention is to embed the markers 11 into the trench 101 so that the markers 11 and inspecting area are located at the same focus plane when the tilted 2D images are acquired. Thereby, the feature tracking process can be performed perfectly with the embedded markers 11 and then improve the 3D image quality.

Figure 2:
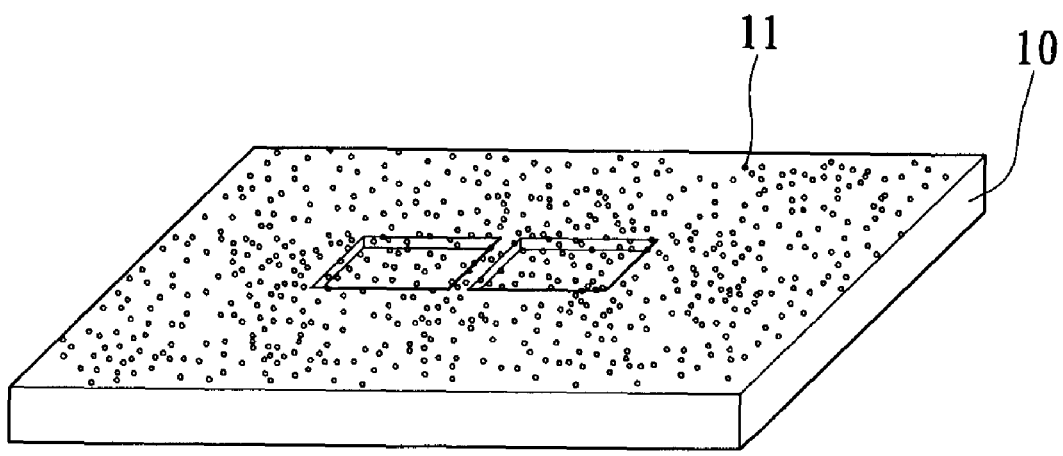
FIG. 2 is a schematic diagram of depositing the markers onto the trenches and surface of the chip of the present invention.

Reference is made to FIG. 2. The present invention provides the gold particles as the markers 11. In fact, the markers 11 can be other metal particles that can show a high contrast in images to be used as the alignment references for reconstructing the 3D image. A liquid with gold beads that the diameter is between 10 nm and 20 nm, such as "protein A" from Jed Pella, Inc., California, USA, is dropped on the surface of the chip 10. The liquid is filled into the two trenches 101, and the gold particles also are filled into the two trenches 101. Next, a proper method is used to remove the organic or biochemical solvent in the protein solution. For example, organic solvent is used for removing the solvent in the protein solution to make the gold beads fill into the two trenches 101. In this step, the markers 11 are spread in the trenches 101 and on the surface of the chip 10. For the inspecting area, the markers 11 are embedded at sides of the inspecting area and spread on the chip's surface.

The present invention does not limit the diameter of the gold beads. However, because the gold beads are used as the alignment references for reconstructing a series of tilted 2D images into a 3D image, and it shall have enough amount of gold beads can be used as references to achieve the best alignment quality. Therefore, the nano-size particles are preferably used so that adequate markers 11 are received in the two trenches 101.

Figure 3:
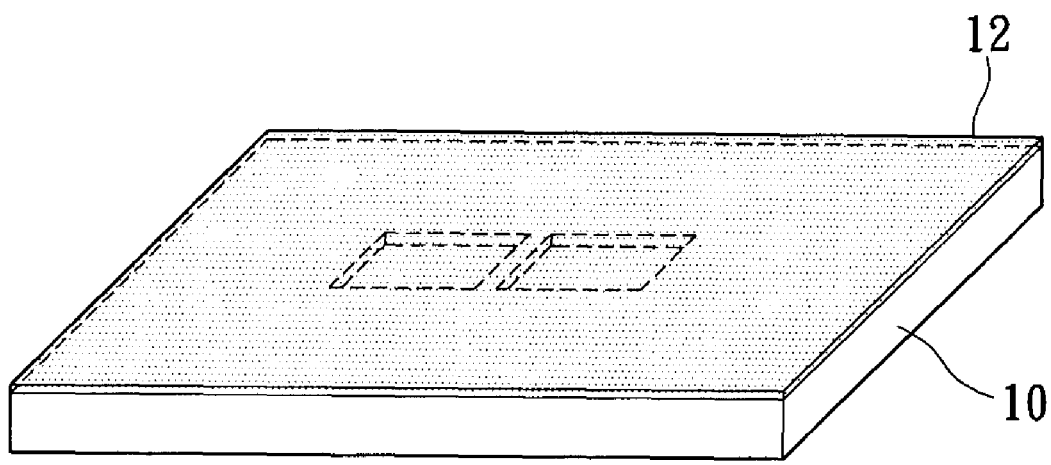
FIG. 3 is a schematic diagram of coating the first protection layer on the chip of the present invention.

Step 4: Reference is made to FIG. 3. A first protection layer 12 is coated on the chip 10. The markers 11 must be fastened and protected. In this step, a polymer layer is coated on the chip 10 to be the first protection layer 12. Moreover, the first protection layer 12 can be filled into the gap between the markers 11, and covers the markers 11 so that the markers 11 are fastened on the proper location.

After the resin material is coated on the chip 10, a solidification process is performed. The resin material is transformed into a solid resin film layer (i.e. first protection layer 12) at a proper temperature and within a proper period.

Figure 4:
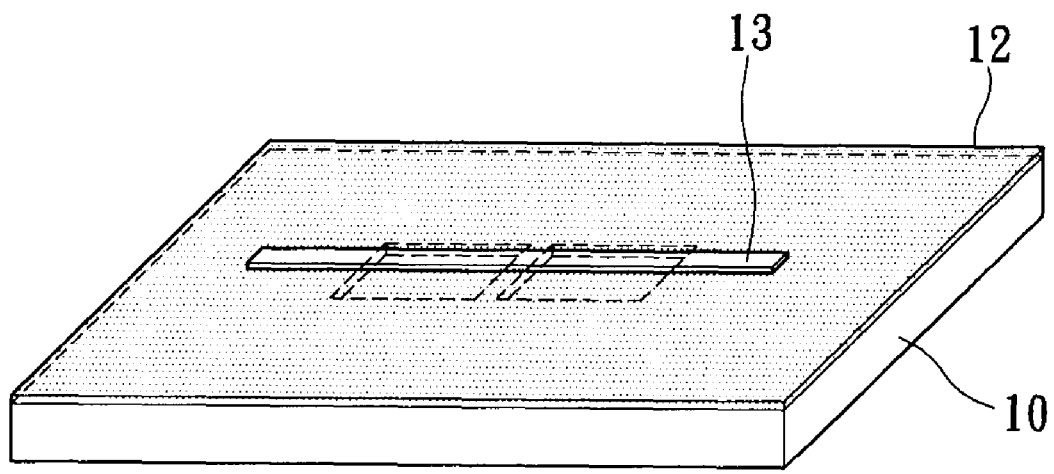
FIG. 4 is a schematic diagram of depositing the second protection layer on the first protection layer of the present invention.

Step 5: Reference is made to FIG. 4. A second protection layer 13 is deposited on the first protection layer 12. Before the chip 10 is inspected by an electron microscope analysis (especially for the TEM), a thinning process by ion beam milling method has to be performed. Therefore, the goal of the second protection layer 13 is to protect the markers 11 and the inspecting area for avoiding the damage during thinning by ion beam milling. In this embodiment, the second protection layer 13 is a metal layer (such as a Pt or W layer), and the second protection layer 13 is not fully covered the chip 10. Only the inspecting area and neighborhood is covered and protected. However, the depositing area of the second protection layer 13 can be adjusted according to the requirement.

After the step 5, a sample thinning process is included to form the ET specimen with interesting area of chip 10. There are two ways to manufacture the ET specimen of chip 10. The first way is the ex-situ lift out method. The ET specimen of chip 10 is manufactured in a DB FIB system and then lifted out away from chip 10 and placed onto carbon-coated grids using a glass needle by electrostatic forces in a plucking system. The second way is the in-situ lift out method. Firstly, a cantilever shape specimen is manufactured on the chip 10. The cantilever's free end is then welded to the needle's tip using Pt in-situ deposition. The cantilever's anchor is next cut to fee it from the chip 10 and a wedge shaped specimen is formed. Following this the wedge shape specimen is lifted out and welded the wedge shape specimen onto the top of half copper ring or copper five post lift-out grids. Next the needle is cut away from the wedge shape specimen and it is moved away from the half copper ring or grids. The wedge shape specimen is then milled into an ET specimen. All the processes of in-situ lift out method are done in a DB FIB system. The cutting process is not limited to above two ways. The goal of the cutting process is to manufacture and place an ET specimen onto the specimen holder for analyzing.

The present invention also provides a second embodiment of the manufacturing method for an ET specimen of chip 10 that includes the following steps.

Step 1: A chip 10 is provided. The chip 10 includes at least one via-hole structure, such as a metal via that is filled with a barrier layer, such as TiN/Ti, and is not filled with the metal. The step coverage of barrier layers is very important to the electrical performance of metal vias. In this embodiment, the via-hole structure is filled with the barrier layer to manufacture the chip 10. In this case, the via-hole is a concave structure that is used for receiving the markers 11.

Next, a liquid with the markers 11 is filled into the via-hole structures. The goal of this step is to fill the markers 11 into the via-hole structures and spread on the surface of chip 10 so that the markers 11 and interest are located at the same focus plane during series of tilted 2D images acquisition. The 2D images are aligned by using the markers 11 so that the 3D image can be reconstructed with high quality. The liquid with the gold beads of this embodiment is the same as the first embodiment, and is not illustrated again. Similarly, the first protection layer 12 and the second protection layer 13 are also the same as the first embodiment.

After the solidification process for the second protection layer 13, a cutting process is included to manufacture an ET specimen. For example, the ex-situ lift out method or the in-situ lift out method is used to manufacture the ET specimen with interesting area on chip 10. The goal of the cutting process is to manufacture and place the ET specimen from chip 10 onto the specimen holder for analyzing (that is the same as the first embodiment). Similarly, the specimen holder can be carbon-coated grids, half copper ring, and copper five post lift-out grids.

The characteristic of the present invention is to embed the markers 11 into the chip 10 (filled into the trenches 101, or the via-hole structure of the chip 10) to be the alignment references for feature tracking process. The quality of the feature tracking process and 3D reconstruction is improved.

After the markers 11 are disposed beside the inspecting area and surface of chip 10, the present invention also provides a method for reconstructing the 3D image after the feature tracking process utilizing the markers 11 that includes the following steps.

Step 1: A chip 10 embedded with the markers 11 is manufactured. This step uses the above processes to embed the markers 11 into the chip 10. The markers 11 are surrounded the inspecting area.

After the steps of embedding the markers 11, forming the first protection layer 12, and forming the second protection layer 13 are finished, a cutting and a thinning process are performed on chip 10, such as the ion beam thinning technology. Finally, the thinned ET specimen of chip 10 is placed on a specific specimen holder, such as carbon-coated grids, half Cu ring or copper five post lift-out grids, to perform series of tilted 2D images acquisition, image processing, and 3D reconstruction.

Step 2: The thinned ET specimen of chip 10 is rotated, and an electron microscope is used to obtain the series of tilted 2D images at different angles. In this step, the specimen holder and the ET specimen are placed in an electron microscope to perform the structure or compositional analysis. In one embodiment, the thinned ET specimen of chip 10 is placed in a transmission electron microscope (but not limited to above), and the thinned ET specimen of chip 10 is rotated to obtain the 2D images at different angles.

Step 3: The markers 11 are used as alignment references to reconstruct series of tilted 2D images at different angles into a 3D image. In this step, all the 2D images at different angles are reconstructed into the 3D image. In this step, the 2D images obtained by the prior art cannot be exactly aligned due to the gap between markers and specimen. On the contrary, the markers 11 embedded in the thinned specimen of chip 10 can be used as alignment references so that the image process software can easily track the markers 11 for each image to solve the problems of change in focus and image shift.

The present invention has the following characteristics:

1. The present invention uses the markers that are located at the same focus plane with the inspection objective to acquire the 2D images at different angles. Therefore, the computer can directly track the markers as the alignment reference to reconstruct the 3D image.

2. Because the present invention embeds the markers into the specimen, the markers and the inspection objective are located at the same focus plane during series of tilted 2D images acquisition. The markers that are clearly focused can be used as a calibration reference for the thickness measurements of structures in 3D image. For example the barrier layer is formed on the wall of the via-hole structures. When the via-hole structures are filled with the markers, the dimension of the markers can be used as a calibration reference to precisely calculate the thickness of the barrier layer in a 3D image.

The description above only illustrates specific embodiments and examples of the present invention. The present invention should therefore cover various modifications and variations made to the herein-described structure and operations of the present invention, provided they fall within the scope of the present invention as defined in the following appended claims.

What is claimed is:

1. A preparation method for an electron tomography specimen with embedded markers, comprising the steps of:
   providing a chip, wherein the chip includes at least one inspecting area;
   producing at least one trench adjacent to the inspecting area;
   filling a liquid with markers into the trench;
   coating a first protection layer on the chip; and
   depositing a second protection layer on the first protection layer.

2. The preparation method as claimed in claim 1, wherein in step of producing at least one trench, the trench is produced by a dual beam focused ion beam system.

3. The preparation method as claimed in claim 1, wherein the markers are metal particles, and the metal particles have a predetermined dimension in step of filling a liquid with markers into the trench.

4. The preparation method as claimed in claim 1, wherein the first protection layer is a polymer layer.

5. The preparation method as claimed in claim 4, further comprising a solidification process of the polymer layer after the step of coating a first protection layer on the chip.

6. The preparation method as claimed in claim 1, wherein the second protection layer is a metal layer.

7. The preparation method as claimed in claim 1, further comprising a cutting process after step of coating a second protection layer on the first protection layer.

8. A preparation method for an electron tomography specimen with embedded markers, comprising the steps of:
   providing a chip, wherein the chip includes at least one via-hole structure;
   filling a liquid with markers into the via-hole structures;
   coating a first protection layer on the chip; and
   depositing a second protection layer on the first protection layer.

9. The preparation method as claimed in claim 8, wherein the markers are metal particles, and the metal particles have a predetermined dimension in step of filling a liquid with markers into the via-hole structures.

10. The preparation method as claimed in claim 8, wherein the first protection layer is a polymer layer.

11. The preparation method as claimed in claim 10, further comprising a solidification process of the polymer layer after step of coating a first protection layer on the chip.

12. The preparation method as claimed in claim 8, wherein the second protection layer is a metal layer.

13. The preparation method as claimed in claim 8, further comprising a cutting process after step of depositing a second protection layer on the first protection layer.

14. A method for reconstructing a 3D image, comprising the steps of:

manufacturing an electron tomography specimen with embedded markers by using the preparation method as claimed in claim 1 or in claim 8;

providing an electron microscope to obtain series of tilted 2D images of the electron tomography specimen at different angles; and using the markers as alignment references to reconstruct the series of tilted 2D images at different angles into a 3D image of the electron tomography specimen.

15. The method for reconstructing a 3D image as claimed in claim 14, further comprising a thinning process to thin the electron tomography specimen after step of manufacturing a microscope sample.

16. The method for reconstructing a 3D image as claimed in claim 15, further comprising a step of placing the electron tomography specimen onto a specimen holder after the thinning process.

17. The method for reconstructing a 3D image as claimed in claim 16, wherein the specimen holder is a carbon-coated grids or a half Cu ring with a convex structure or a copper five post lift-out grids.

18. The method for reconstructing a 3D image as claimed in claim 14, wherein the markers are metal particles, and the metal particles have a predetermined dimension.

\* \* \* \* \*